US012765944B2

(12) United States Patent
Takahashi

(10) Patent No.: US 12,765,944 B2
(45) Date of Patent: Oct. 20, 2026

(54) MEDICAL DEVICE WITH EXPANSION BODY AND ELASTICALLY DEFORMABLE PART

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 287 days.

(21) Appl. No.: 18/461,982

(22) Filed: Sep. 6, 2023

(65) Prior Publication Data

US 2023/0404665 A1 Dec. 21, 2023

Related U.S. Application Data

(63) Continuation of application No. PCT/JP2022/009469, filed on Mar. 4, 2022.

(30) Foreign Application Priority Data

Mar. 8, 2021 (JP) ................................ 2021-036374

(51) Int. Cl.
*A61B 18/14* (2006.01)
*A61B 17/00* (2006.01)
*A61B 18/00* (2006.01)

(52) U.S. Cl.
CPC *A61B 18/1492* (2013.01); *A61B 2017/00247* (2013.01); *A61B 2017/00862* (2013.01);
(Continued)

(58) Field of Classification Search
CPC ...... A61B 18/1492; A61B 2017/00247; A61B 2017/00862; A61B 2018/0016;
(Continued)

(56) References Cited

U.S. PATENT DOCUMENTS 6,375,650 B1 4/2002 Ouchi
2018/0289388 A1 10/2018 Lenker et al.
(Continued)

FOREIGN PATENT DOCUMENTS

CN 112716557 A 4/2021
JP S56-52886 Y2 12/1981
(Continued)

OTHER PUBLICATIONS

International Search Report (PCT/ISA/210) with English translation and Written Opinion (PCT/ISA/237) mailed on May 17, 2022, by the Japanese Patent Office as the International Searching Authority for International Application No. PCT/JP2022/009469.
(Continued)

*Primary Examiner* — Tigist S Demie
(74) *Attorney, Agent, or Firm* — BUCHANAN INGERSOLL & ROONEY PC

(57) ABSTRACT

A medical device that is configured to stably hold and expand biological tissue through a certain amount of pulling operation by ways of an expansion body includes: an expansion body expandable and contractible in a radial direction; an elongated shaft portion that includes a distal end part including a proximal end fixing portion to which a proximal end of the expansion body is fixed; and a hand operation unit disposed on a proximal side of the shaft portion. The shaft portion includes a pulling shaft that moves in an axial direction to compress the expansion body in an axial direction. The hand operation unit includes a pulling operation unit that moves the pulling shaft in the axial direction. The pulling shaft and the pulling operation unit are connected to each other with a buffer portion therebetween, the buffer portion being elastically deformable along the axial direction of the pulling shaft.

19 Claims, 8 Drawing Sheets

(52) U.S. Cl.
CPC ................. *A61B 2018/0016* (2013.01); *A61B 2018/00267* (2013.01); *A61B 2018/00357* (2013.01); *A61B 2018/00595* (2013.01); *A61B 2018/142* (2013.01)

(58) Field of Classification Search
CPC ........... A61B 2018/00196; A61B 2018/00267; A61B 2018/00357; A61B 2018/0038; A61B 2018/00577; A61B 2018/00595; A61B 2018/142
See application file for complete search history.

(56) References Cited

U.S. PATENT DOCUMENTS

| | | | |
|---|---|---|---|
| 2020/0170662 A1 | 6/2020 | Vardi et al. | |
| 2021/0001116 A1* | 1/2021 | Waldhauser | A61B 34/25 |
| 2021/0007791 A1* | 1/2021 | Takahashi | A61B 18/1492 |

FOREIGN PATENT DOCUMENTS

| | | | |
|---|---|---|---|
| JP | 3718372 | B2 | 11/2005 |
| JP | 4982699 | B2 | 7/2012 |
| WO | 2006/078743 | A1 | 7/2006 |
| WO | 2019138321 | A1 | 7/2019 |
| WO | 2019188916 | A1 | 10/2019 |
| WO | 2020094087 | A1 | 5/2020 |

OTHER PUBLICATIONS

Extended European Search Report issued on Oct. 16, 2024 by the European Patent Office in corresponding European Patent Application No. 22767033.8. (7 pages).
Office Action (Notice of Reasons for Refusal) issued on Jul. 22, 2025, in corresponding Japanese Patent Application No. 2023-505507 and machine English translation of the Office Action. (16 pages).

* cited by examiner

FIG. 10
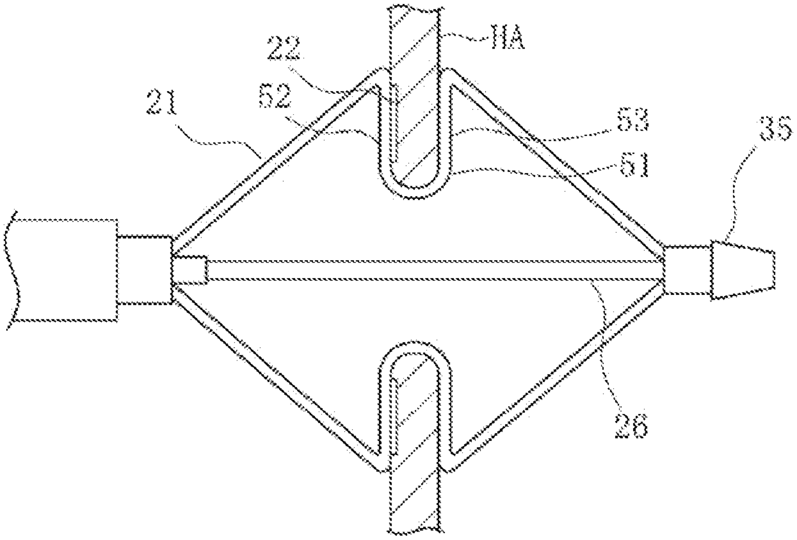
FIG. 11a
FIG. 11b
FIG. 11c
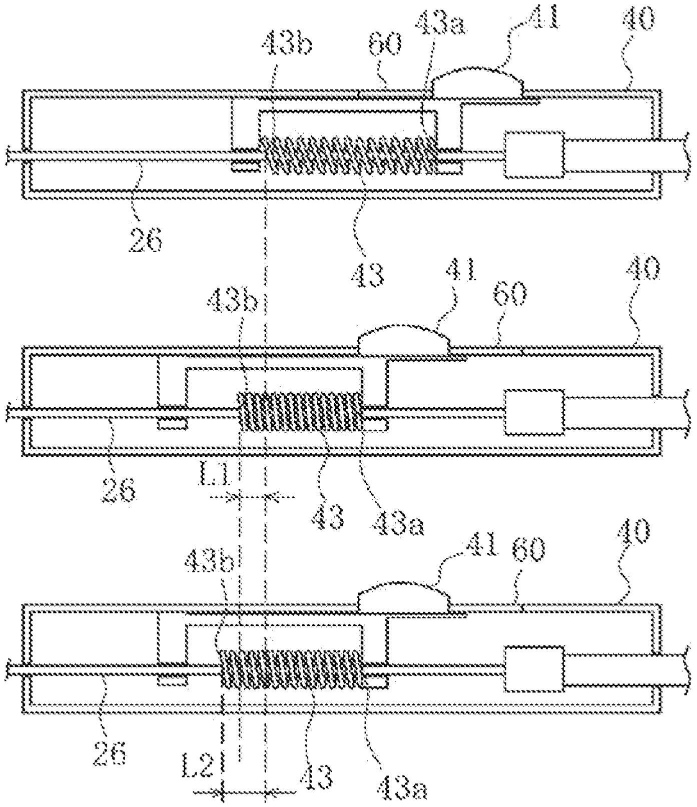

MEDICAL DEVICE WITH EXPANSION BODY AND ELASTICALLY DEFORMABLE PART

CROSS-REFERENCES TO RELATED APPLICATIONS

This application is a continuation of International Patent Application No. PCT/JP2022/009469 filed on Mar. 4, 2022, which claims priority to Japanese Patent Application No. 2021-036374 filed on Mar. 8, 2021, the entire content of both of which is incorporated herein by reference.

TECHNOLOGICAL FIELD

The present invention generally relates to a medical device including an expansion body that expands and contracts by movement of a pulling shaft in an axial direction.

BACKGROUND DISCUSSION

As a medical device, there is a device including an expansion body that expands and contracts in a living body. For example, a medical device is known that includes an electrode portion provided on an expansion body, and performs treatment by ablation for cauterizing a biological tissue by a high-frequency current from the electrode portion. As one type of ablation treatment, a shunt treatment on the atrial septum is known. The shunt treatment can alleviate heart failure symptoms of a patient with heart failure by forming a shunt (puncture hole) serving as an escape route for increased atrial pressure in the atrial septum of the patient. In the shunt treatment, the atrial septum is accessed using an intravenous approaching method, and a puncture hole with a desired size is formed. Such a medical device is disclosed in, for example, International Patent Application Publication No. 2020/94087 (WO 2020/94087 A).

SUMMARY

An expansion body disclosed in International Patent Application Publication No. 2020/94087 can self-expand by being exposed from a sheath. The expanded expansion body holds a biological tissue. In this case, the holding force and expansion force may vary greatly depending on the thickness and hardness of the biological tissue. When a medical device provided with an electrode portion at a holding portion holds a biological tissue with weak holding force, the electrode portion cannot sufficiently come into contact with the biological tissue, resulting in causing a risk of cauterization failure and thrombus formation. In addition, when holding force for holding the biological tissue is strong, there is a risk of physically damaging the biological tissue. Furthermore, when the expansion force is weak, the expansion body cannot be expanded with a desired expansion amount, and when the expansion force is strong, the expansion body is excessively expanded with an amount beyond the desired expansion amount.

The medical device disclosed here can stably hold and expand a biological tissue with an expansion body by a certain amount of pulling operation.

According to one aspect, a medical device includes: an expansion body expandable and contractible in a radial direction; a shaft portion that is elongated and includes a distal end part including a proximal end fixing portion to which a proximal end of the expansion body is fixed; and a hand operation unit disposed on a proximal side of the shaft portion, in which the shaft portion includes a pulling shaft that moves in an axial direction to compress the expansion body in the axial direction, the hand operation unit includes a pulling operation unit that moves the pulling shaft in the axial direction, and the pulling shaft and the pulling operation unit are connected to each other with a buffer portion interposed between the pulling shaft and the pulling operation unit, the buffer portion being elastically deformable along the axial direction of the pulling shaft.

In the medical device configured as described above, the pulling shaft is pulled by the pulling operation unit via the buffer portion. Therefore, when the pulling operation unit is operated to move by a certain amount, the buffer portion is elastically deformed according to the thickness and hardness of the biological tissue with which the expansion body is in contact, and thus, a constant pulling force can be applied to the expansion body regardless of the state of the biological tissue. Accordingly, the biological tissue can be stably held and expanded by the expansion body.

The buffer portion may include a distal end part and a proximal end part on a side opposite to the distal end part, the pulling operation unit may include a pulling operation unit-side fixing portion fixed to one of the distal end part and the proximal end part of the buffer portion, the pulling shaft may include a pulling shaft-side fixing portion fixed to another of the distal end part and the proximal end part of the buffer portion, and the pulling operation unit-side fixing portion and the pulling shaft-side fixing portion may be disposed along the axial direction of the pulling shaft. With this configuration, the pulling operation unit, the buffer portion, and the pulling shaft can be compactly accommodated.

The pulling operation unit-side fixing portion may be fixed to the distal end part of the buffer portion, the pulling shaft-side fixing portion may be fixed to the proximal end part of the buffer portion, and the buffer portion may be elastically deformed in a compression direction by moving the pulling operation unit from a distal side to a proximal side along the axial direction of the pulling shaft. With this configuration, a constant pulling force can be applied to the expansion body with a simple structure in which the buffer portion is elastically deformed in the compression direction.

The buffer portion may be a coil spring through which the pulling shaft is insertable. With this configuration, the pulling shaft and the buffer portion can be coaxially disposed, whereby the structure in the hand operation unit can be made compact.

The buffer portion may be a single or a plurality of coil springs disposed in parallel with the pulling shaft. With this configuration, the buffer portion can be attached to the pulling shaft from the side, whereby assembly can be facilitated.

The pulling operation unit-side fixing portion may be fixed to the proximal end part of the buffer portion, the pulling shaft-side fixing portion may be fixed to the distal end part of the buffer portion, and the buffer portion may be elastically deformed in an extending direction by moving the pulling operation unit from a distal side to a proximal side along the axial direction of the pulling shaft. With this configuration, a constant pulling force can be applied to the expansion body with a simple structure in which the buffer portion is elastically deformed in the extending direction.

A part or whole of the pulling shaft may be elastically deformable along the axial direction of the pulling shaft. With this configuration, the pulling shaft can be used as the buffer portion, whereby the structure can be further simplified.

The buffer portion may be disposed inside the hand operation unit. With this configuration, the structure of the shaft portion can be prevented from being complicated.

Another aspect involves a medical device operated by an operator to cauterize an edge of a puncture hole in a living body. The medical device comprises: an expansion body positionable in the puncture hole in the living body and having opposite axial end portions that are relatively movable so that as the opposite axial end portions approach one another the expansion body expands radially outwardly towards the edge of the puncture hole in the living body, and as the opposite axial end portions approach one another the expansion body contracts radially inwardly away from the edge of the puncture hole in the living body; an energy transfer element positioned on the expansion body and movable into contact with the edge of the puncture hole in the living body as the expansion body expands radially outwardly to transfer energy to the edge of the puncture hole in the living body and cauterize the edge of the puncture hole; an elongated outer tube having a distal end portion fixed to the proximal end portion of the expansion body; and a shaft positioned in the elongated outer tube. The shaft is axially movable in an axial direction relative to the elongated outer tube and includes a portion that extends distally beyond the distal end portion of the elongated outer tube, with the portion of the shaft being fixed to the distal end portion of the expansion body. An elastically deformable part moves together with the shaft in the axial direction and is elastically deformable in the axial direction, an upstanding operation part is engageable by the operator to slidably move the upstanding operation part in a proximal direction, and the shaft and the upstanding operation part are connected to each other with the elastically deformable part positioned between the shaft and the upstanding operation part so that sliding movement of the upstanding operation part in the proximal direction results in axial movement of the shaft in the proximal direction and elastic deformation of the elastically deformable part, with the axial movement of the shaft in the proximal direction causing the opposite axial end portions of the expansion body to approach one another so that the expansion body expands radially outwardly.

Another aspect involves a medical device operated by an operator to cauterize a puncture hole in a living body. The medical device comprises: an expansion body positionable in the puncture hole in the living body and having opposite axial end portions that are relatively movable so that as the opposite axial end portions approach one another the expansion body expands radially outwardly towards the edge of the puncture hole in the living body, and as the opposite axial end portions approach one another the expansion body contracts radially inwardly away from the edge of the puncture hole in the living body; an electrode positioned on the expansion body to contact an edge of the puncture hole in the living body as the expansion body expands radially outwardly to cauterize the edge of the puncture hole; an elongated outer tube having a distal end portion fixed to the proximal end portion of the expansion body; and a shaft positioned in the elongated outer tube. The shaft is axially movable in an axial direction relative to the elongated outer tube and includes a portion that extends distally beyond the distal end portion of the elongated outer tube. The portion of the shaft that extends distally beyond the distal end portion of the elongated outer tube is fixed to the distal end portion of the expansion body. The medical device also comprises a housing having an interior through which passes the shaft, and a manually engageable part that is slidably mounted on the housing and that is manually engageable by the operator to slidably move the manually engageable part in a rearward direction relative to the housing. The manually engageable part is operatively connected to the shaft by way of an elastically deformable part so that sliding movement of the manually engageable part in the rearward direction results in movement of the shaft in the rearward direction and elastic deformation of the elastically deformable part.

BRIEF DESCRIPTION OF THE DRAWINGS

FIGS. 6*a* and 6*b* are diagrams illustrating a state in S2 in FIG. 5, in which FIG. 6*a* is an enlarged view of the vicinity of a balloon in the atrial septum illustrated in cross section, and FIG. 6*b* is a cross-sectional view of the atrial septum for describing a shape of a puncture hole.

FIGS. 7*a* and 7*b* are diagrams illustrating a state in S3 in FIG. 5, in which FIG. 7*a* is an enlarged view of the vicinity of the expansion body illustrating the atrial septum in cross section and the inside of a storage sheath in a transparent manner, and FIG. 7*b* is a cross-sectional view of the atrial septum in a state where the storage sheath is inserted through the puncture hole.

FIG. 10 is a diagram illustrating a state in S5 in FIG. 5, and is an enlarged view of the vicinity of the expansion body in the atrial septum illustrated in cross section.

FIGS. 11*a*-11*c* are front views illustrating an internal structure of the hand operation unit, in which FIG. 11*a* is a diagram illustrating a state before a pulling operation, FIG. 11*b* is a diagram illustrating a state in which a buffer portion is greatly compressed by the pulling operation, and FIG. 11*c* is a diagram illustrating a state in which the buffer portion is slightly compressed by the pulling operation.

DETAILED DESCRIPTION

Figure 1:
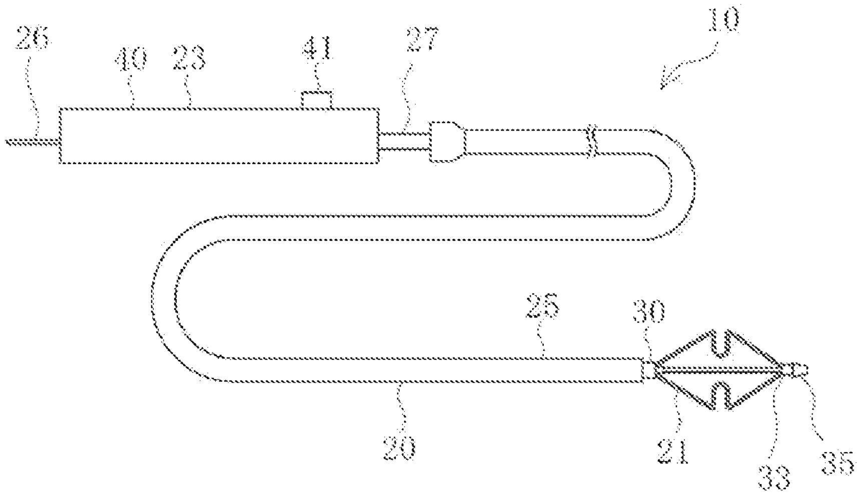
FIG. 1 is a front view illustrating an overall configuration of a medical device according to an embodiment.

Set forth below with reference to the accompanying drawings is a detailed description of embodiments of a medical device representing examples of the new medical device disclosed here. Dimensional ratios in the drawings may be exaggerated and different from actual ratios for convenience of description. In addition, in the present specification, a side on which a medical device 10 is inserted into a biological lumen will be referred to as "distal end" or "distal side", and a side operated by an operator will be referred to as "proximal end" or "proximal side".

The medical device according to the embodiment described below is configured to expand a puncture hole Hh formed in an atrial septum HA of the heart H of a patient, and to further perform a maintenance treatment to keep the expanded puncture hole Hh at the increased size.

As illustrated in FIG. 1, the medical device 10 according to the present embodiment includes an elongated shaft portion 20, an expansion body 21 disposed at a distal end part of the shaft portion 20, and a hand operation unit 23 disposed at a proximal end part of the shaft portion 20. The expansion body 21 has an electrode portion 22 which is an energy transfer element for performing the above-described maintenance treatment.

The shaft portion 20 has a distal end part 30 including a proximal end fixing portion 31 to which a proximal end of the expansion body 21 is fixed and a distal end fixing portion 33 to which a distal end of the expansion body 21 is fixed. The shaft portion 20 has a storage sheath 25 disposed at an outermost peripheral portion. The expansion body 21 is movable forward and rearward in an axial direction relative to the storage sheath 25. The storage sheath 25 can accommodate the expansion body 21 therein in a state of moving to the distal side of the shaft portion 20. The expansion body 21 can be exposed by moving the storage sheath 25 that has accommodated the expansion body 21 to the proximal side.

The shaft portion 20 includes an outer tube 27 extending from the hand operation unit 23 to the proximal end fixing portion 31, and a pulling shaft 26 stored inside the outer tube 27. The pulling shaft 26 extends from the proximal end of the shaft portion 20 to a distal member 35 within the outer tube 27, and the distal end part thereof is fixed to the distal member 35.

The distal member 35 to which the distal end part of the pulling shaft 26 is fixed may not be fixed to the expansion body 21. Accordingly, the distal member 35 can pull the expansion body 21 in a contracting direction. In addition, when the expansion body 21 is stored in the storage sheath 25, the distal member 35 is separated to the distal side from the expansion body 21, by which the expansion body 21 can be rather easily moved in an axial direction. Thus, ease of storage can be improved.

Figure 3:
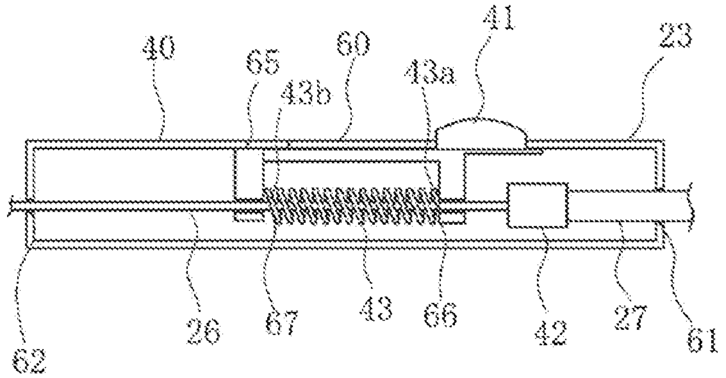
FIG. 3 is a front view illustrating an internal structure of a hand operation unit.

The hand operation unit 23 includes a housing 40 gripped by the operator and a pulling operation unit 41 that can be operated by the operator. FIG. 3 shows that the pulling operation unit 41 may be an upstanding or projecting operation part that is operable by the operator. As illustrated in FIG. 3, the housing 40 includes a slit 60 through which the pulling operation unit 41 is slidably inserted or slidably positioned, an outer tube insertion opening 61 through which the outer tube 27 is inserted or passes, and a pulling shaft insertion opening 62 through which the pulling shaft 26 is inserted or passes. The outer tube 27 inserted into or passing through the outer tube insertion opening 61 is fixed to an outer tube holding portion 42 disposed in the housing 40. The pulling shaft 26 extends to the proximal side from the outer tube holding portion 42 and is led out from the proximal end of the housing 40 in the proximal direction. The pulling operation unit 41 includes a slide portion 65 slidably held in the housing 40.

A buffer portion 43 is provided between the pulling operation unit 41 and the pulling shaft 26. The buffer portion 43 includes a coil spring elastically deformable along the length direction so that the buffer portion 43 is an elastically deformable part or structure. A distal end part **43*a* of the buffer portion 43 is fixed to a pulling operation unit-side fixing portion 66 formed by the pulling operation unit 41 extended into the housing 40. A proximal end part 43*b* of the buffer portion 43 is fixed to a pulling shaft-side fixing portion 67 of the pulling shaft 26. The pulling operation unit 41 slides toward the proximal side from the state of FIG. 3, and thus, the buffer portion 43 having the distal end part 43*a* fixed to the pulling operation unit 41 and the proximal end part 43*b* fixed to the pulling shaft 26** can be elastically deformed in the compression direction.

Figure 2:
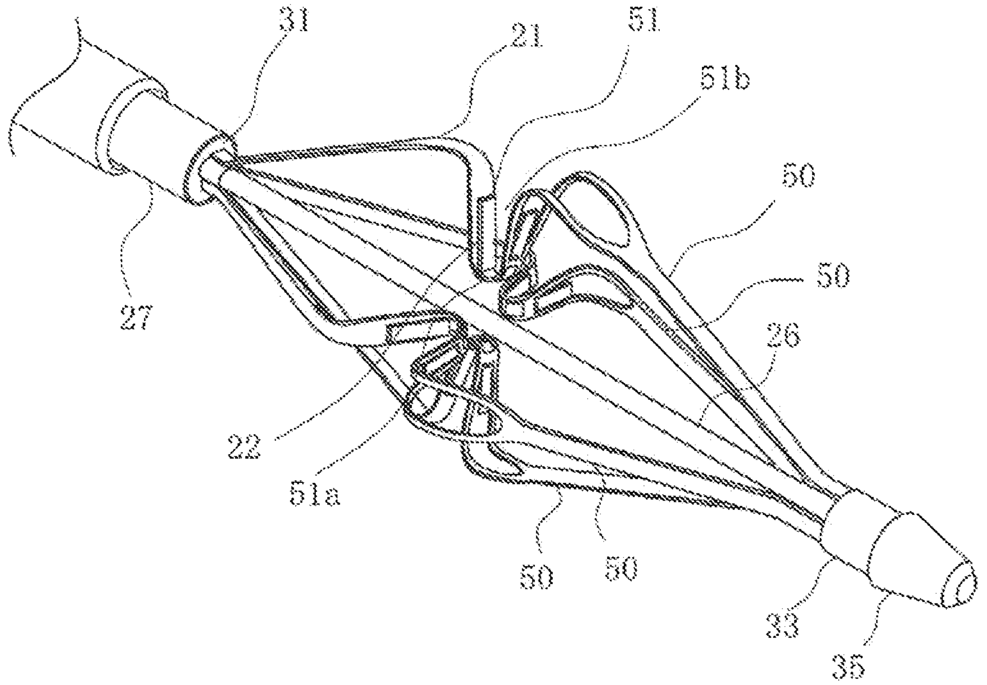
FIG. 2 is an enlarged perspective view illustrating the vicinity of an expansion body.

As illustrated in FIG. 2, the expansion body 21 has a plurality of wire portions in a circumferential direction. In the present embodiment, four wire portions 50 are disposed in the circumferential direction. Each of the wire portions 50 is configured to expand and contract in a radial direction. A proximal end part of the wire portion 50 extends to the distal side from the proximal end fixing portion 31. A distal end part of the wire portion 50 extends to the proximal side from a proximal end part of the distal end fixing portion 33. The wire portion 50 is inclined to increase (expand) in the radial direction from both ends toward a central part in the axial direction. In addition, the wire portion 50 has a recess 51 in the central part in the axial direction, the recess 51 being recessed radially inward of the expansion body 21. An innermost part of the recess 51 in the radial direction is a bottom portion **51*a*. The recess 51 defines a reception space 51*b* configured to receive a biological tissue when the expansion body 21 expands. The electrode portion 22 is disposed in the recess 51 so as to face the reception space 51*b***.

The wire portion 50 forming the expansion body 21 has, for example, a flat plate shape cut from a cylinder. The wire forming the expansion body 21 can have a thickness in a range of 50 μm to 500 μm and a width in a range of 0.3 mm to 2.0 mm. However, the wire may have dimensions outside these ranges. In addition, the wire portion 50 may have a circular shape in a cross section, or may have other shapes in a cross section.

The electrode portion 22 includes, for example, a bipolar electrode that receives electric energy from an energy supply device (not illustrated) serving as an external device. In this case, electricity is conducted between the electrode portions 22 disposed on the wire portions 50. The electrode portion 22 and the energy supply device are connected to each other by a conductive wire (not illustrated) coated with an insulating coating material. The conductive wire is drawn out to the outside via the shaft portion 20 and the hand operation unit 23, and is connected to the energy supply device.

Alternatively, the electrode portion 22 may be configured as a monopolar electrode. In this case, electricity is supplied from a counter electrode plate prepared outside a body. In addition, a heating element (electrode chip) that generates heat by receiving high-frequency electric energy from the energy supply device may be used instead of the electrode portion 22. In this case, electricity is conducted between the heating elements disposed on the wire portions 50. Furthermore, the electrode portion 22 can be constituted by an energy transfer element configured to apply energy to the puncture hole Hh, such as a heater including an electric wire which provides heating and cooling operation or generating frictional heat by using microwave energy, ultrasound energy, coherent light such as laser, a heated fluid, a cooled fluid, or a chemical medium. A specific form of the energy transfer element is not particularly limited.

The wire portion 50 can be formed of a metal material. Examples of the metal material which can be used include a titanium-based (Ti—Ni, Ti—Pd, or Ti—Nb—Sn) alloy, a copper-based alloy, stainless steel, 6-titanium steel, and a Co—Cr alloy. An alloy having a spring property such as a nickel titanium alloy may be more preferably used. However, a material of the wire portion 50 is not limited to the above materials, and the wire portion 50 may be formed of other materials.

It is preferable that the shaft portion 20 is formed of a material having a certain degree of flexibility. Examples of such a material include polyolefin such as polyethylene, polypropylene, polybutene, ethylene-propylene copolymer, ethylene-vinyl acetate copolymer, ionomer, or a mixture of two or more of them, soft polyvinyl chloride resin, polyamide, polyamide elastomer, polyester, polyester elastomer, polyurethane, fluorine resin such as polytetrafluoroethylene, polyimide, PEEK, silicone rubber, and latex rubber.

The pulling shaft 26 can be formed of, for example, an elongated wire material including a super elasticity alloy such as a nickel-titanium alloy and a copper-zinc alloy, a metal material such as stainless steel, and a resin material having comparatively high rigidity.

The distal member 35 can be formed of, for example, a super elasticity alloy such as a nickel-titanium alloy or a copper-zinc alloy, a metal material such as stainless steel, a polymer material such as polyolefin, polyvinyl chloride, polyamide, polyamide elastomer, polyurethane, polyurethane elastomer, polyimide, and fluororesin or a mixture of the above polymer materials. Alternatively, the distal member 35 can be formed of a multilayer tube containing two or more kinds of polymer materials.

Figure 4:
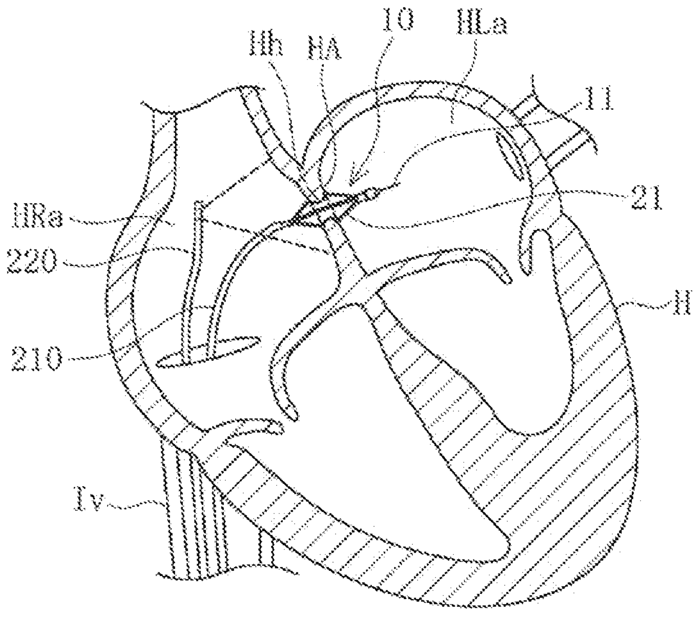
FIG. 4 is an explanatory diagram for schematically describing a state in which the expansion body is placed in the atrial septum, FIG. 4 including a front view of the medical device and a cross-sectional view of a biological tissue.

A treatment method using the medical device 10 will be described. The treatment method according to the present embodiment is performed on a patient suffering from a heart failure (left heart failure). More specifically, the treatment method is performed on the patient with a chronic heart failure having a high blood pressure in a left atrium HLa due to myocardial hypertrophy appearing in a left ventricle of the heart H and increased stiffness (hardness) as illustrated in FIG. 4.

Figure 5:
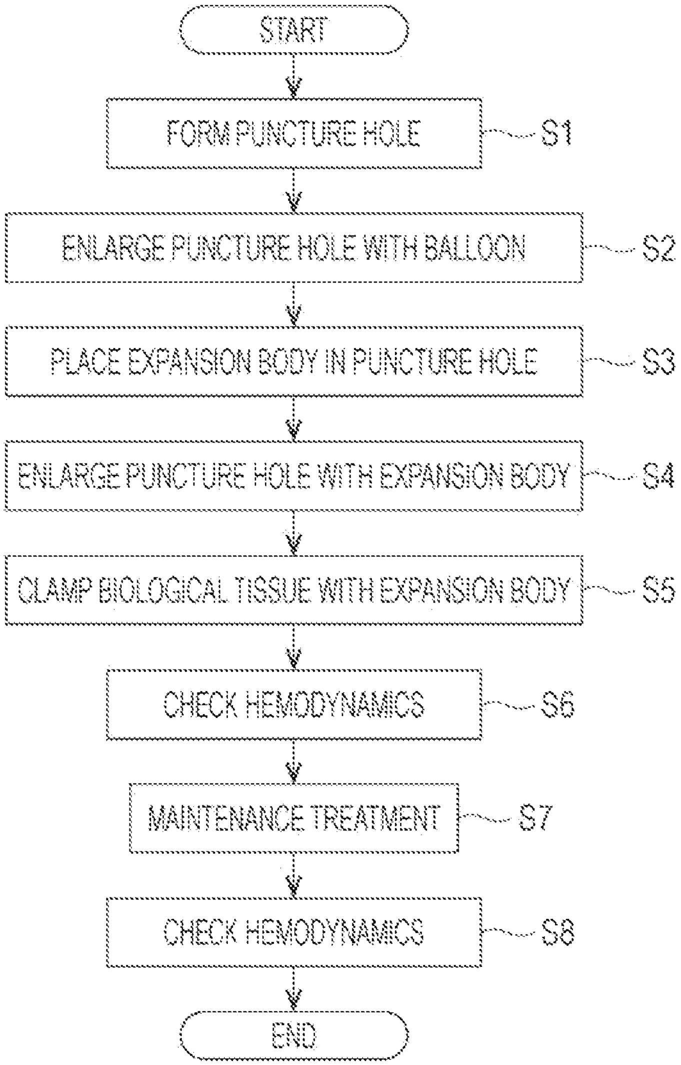
FIG. 5 is a flowchart of a treatment using the medical device.

First, a puncture hole Hh is formed in the atrial septum HA (S1) as illustrated in FIG. 5. In order to form the puncture hole Hh, an operator delivers an introducer 210 obtained by combining a guiding sheath and a dilator to the vicinity of the atrial septum HA. The introducer 210 can be delivered to a right atrium HRa via, for example, an inferior vena cava Iv. In addition, the introducer can be delivered using the guide wire 11. The operator can insert the guide wire 11 into the dilator and deliver the introducer along the guide wire 11. The introducer and the guide wire 11 can be inserted into a living body with a known method such as a method for using an introducer to be introduced into a blood vessel.

The operator inserts a puncture device (not illustrated) so that the puncture device penetrates from the right atrium HRa side toward the left atrium HLa side, thereby forming the puncture hole Hh. The puncture device is inserted into the dilator and delivered to the atrial septum HA.

Figure 6A:
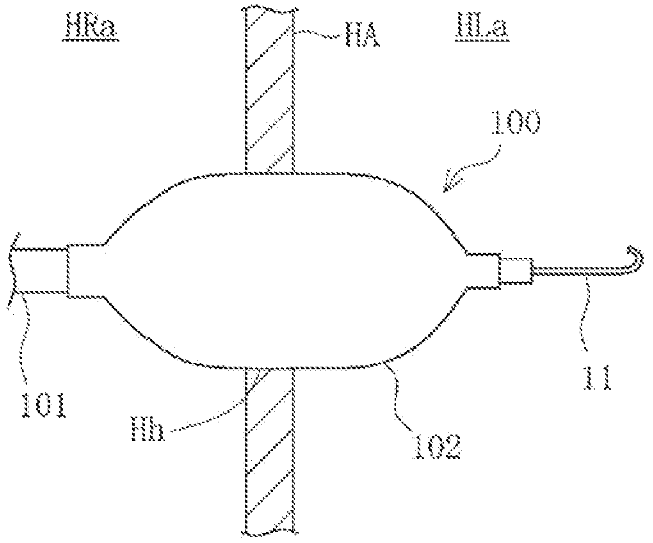
Figure 6B:
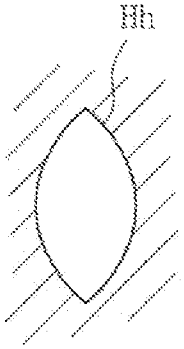

Next, the operator delivers a balloon catheter 100 to the vicinity of the atrial septum HA along the guide wire 11 inserted in advance. The balloon catheter 100 includes a balloon 102 at a distal end part of a shaft portion 101 as illustrated in FIG. 6. After placing the balloon 102 in the atrial septum HA, the operator expands the balloon in the radial direction to enlarge the puncture hole Hh (S2) as illustrated in FIG. 6*a*. During this process, the puncture hole Hh is enlarged to a size equal to the maximum diameter of the expanded balloon 102 in the direction along fibers of the septal tissue due to the influence of the fibers, but is less likely to enlarge in other directions. Therefore, the puncture hole Hh has an elongated shape as illustrated in FIG. 6*b*.

Figure 7A:
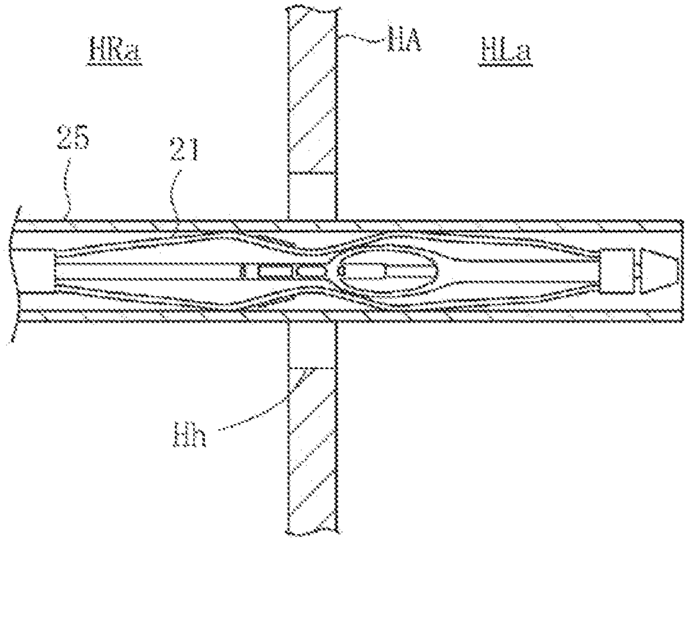
Figure 7B:
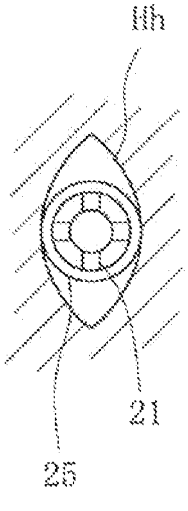

Next, the operator delivers the medical device 10 to the vicinity of the atrial septum HA and places or locates the expansion body 21 at the position of the puncture hole Hh (S3). Although the guide wire is not used for the delivery of the medical device the guide wire may be used for stable operation with the heart beating. At this time, the distal end part of the medical device 10 penetrates the atrial septum HA and reaches the left atrium HLa. In addition, when the medical device 10 is inserted, the expansion body 21 is in a state of being stored in the storage sheath 25 as illustrated in FIG. 7*a*. Since the puncture hole Hh is enlarged by the balloon 102, the storage sheath can be inserted into the puncture hole Hh as illustrated in FIG. 7*b*.

Figure 8:
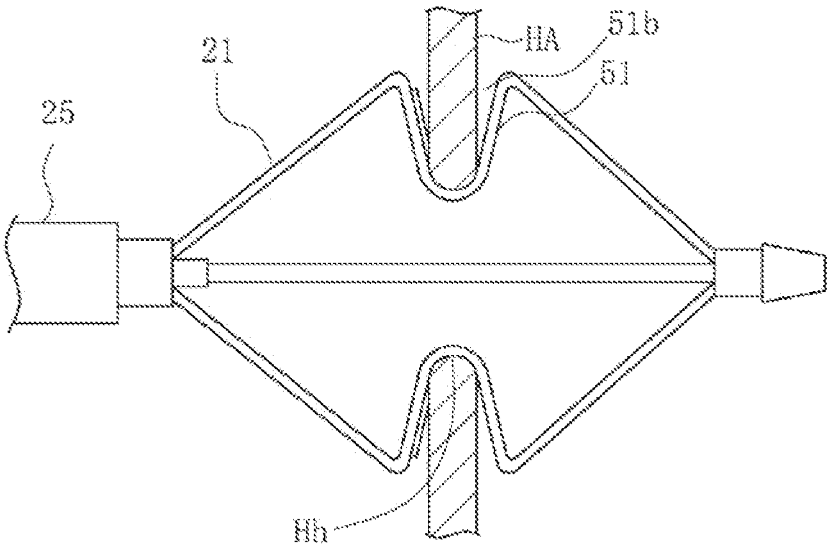
FIG. 8 is a diagram illustrating a state in S4 in FIG. 5, and is an enlarged view of the vicinity of the expansion body in the atrial septum illustrated in cross section.
Figure 9:
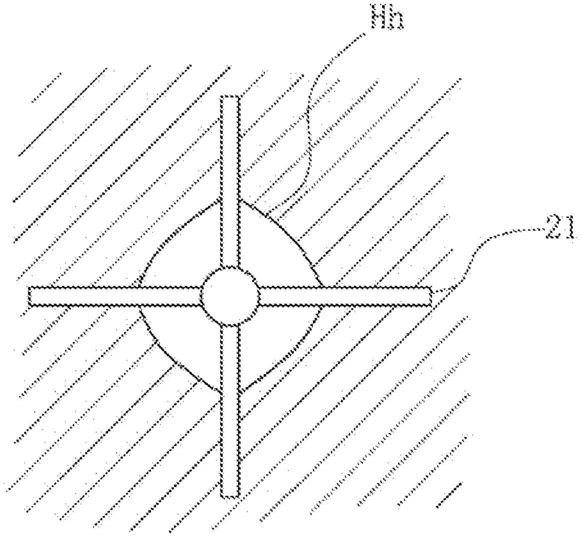
FIG. 9 is a diagram illustrating a state in S4 in FIG. 5, and is a cross-sectional view of the atrial septum in a state where the puncture hole is enlarged with the expansion body.

Next, the operator moves the storage sheath 25 to the proximal side, thereby exposing the expansion body 21 as illustrated in FIG. 8. In this manner, the expansion body 21 increases in diameter, and the recess 51 is located in the puncture hole Hh of the atrial septum HA and receives the biological tissue surrounding the puncture hole Hh in the reception space 51*b* (S4). Due to the expansion of the expansion body 21, the puncture hole Hh is enlarged to have a substantially uniform diameter along the circumferential direction as illustrated in FIG. 9. The expansion body 21 changes the shape of the puncture hole Hh, but does not increase the maximum diameter. Therefore, the maximum diameter of the puncture hole Hh is equal to the diameter of the puncture hole Hh enlarged by the balloon 102 in S2 in the major axis direction.

The operator operates the hand operation unit 23 while the biological tissue is received or located in the reception space 51*b*, and moves the pulling shaft 26 to the proximal side. With this operation, the expansion body 21 is compressed in the axial direction by being pulled in the compression direction by the distal member 35, so that the atrial septum HA is held by the proximal-side upright portion 52 and the distal-side upright portion 53, and the electrode portion 22 is pressed against the biological tissue (S5) as illustrated in FIG. 10.

Before being operated, the pulling operation unit 41 is located at the distal end of the slit 60 as illustrated in FIG. 11*a*. The operator slides the pulling operation unit 41 to the proximal end of the slit 60, so that the pulling shaft 26 moves to the proximal side and the buffer portion 43 is elastically deformed in the compression direction as illustrated in FIG. 11*b*. When the pulling shaft 26 starts to be moved to the proximal side, the pulling shaft 26 moves to the proximal side, whereby the expansion body 21 is compressed in the axial direction to clamp the biological tissue. Until the expansion body 21 clamps the biological tissue, the reaction force against the pulling by the pulling shaft 26 is small, so that the deformation of the buffer portion 43 is small, and the pulling shaft 21 moves to the proximal side. When the expansion body 21 clamps the biological tissue, the reaction force against the pulling by the pulling shaft 26 increases. Therefore, when the pulling operation unit 41 further moves to the proximal side, the buffer portion 43 is elastically deformed in the compression direction by the force. In this manner, the force for operating the pulling operation unit 41 is distributed into the force for elastically deforming the buffer portion 43 and the force for compressing the expansion body 21. As a result, the pulling shaft 26 moves to the proximal side by a distance L1 illustrated in FIG. 11*b*.

When the thickness of the biological tissue received in the reception space 51*b* is thin, the moving distance of the pulling shaft 26 until the expansion body 21 clamps the biological tissue is larger. Therefore, even if the amount of sliding movement of the pulling operation unit 41 is the same as that in the case of FIG. 11*b*, the compression amount of the buffer portion 43 is smaller as illustrated in FIG. 11*c*. In this case, the pulling shaft 26 moves to the proximal side by a distance L2 illustrated in FIG. 11*c*. L2 is larger than L1, that is, as the thickness of the biological tissue is thinner, the pulling shaft 26 moves further to the proximal side, and the expansion body 21 clamps the biological tissue. As described above, even if the movement amount of the pulling operation unit 41 is constant, the pulling shaft 26 moves further to the proximal side by the action of the buffer portion 43 when the biological tissue is thin than when the biological tissue is thick, and the biological tissue can be stably clamped. In addition, even in a case where the biological tissue is thick, the buffer portion 43 is elastically deformed more largely to suppress the movement of the pulling shaft 26. Therefore, even if the amount of movement of the pulling operation unit 41 is constant, it is possible to prevent the expansion body 21 from physically damaging the biological tissue by clamping the biological tissue with an excessive force or from enlarging the puncture hole Hh excessively to be larger than the target.

After enlarging the puncture hole Hh, the operator checks hemodynamics (S6). The operator delivers a hemodynamics checking device 220 to the right atrium HRa by way of the inferior vena cava Iv as illustrated in FIG. 4. As the hemodynamics checking device 220, a known echo catheter can be used, for example. The operator can display an echo image acquired by the hemodynamics checking device 220 on a display device such as a display, and can check an amount of blood passing through the puncture hole Hh on the basis of the displayed echo image.

Next, the operator performs the maintenance treatment for maintaining the size of the puncture hole Hh (S7). During the maintenance treatment, high-frequency energy is applied to an edge of the puncture hole Hh through the electrode portion 22 to cauterize (heat and cauterize) the edge of the puncture hole Hh by the high-frequency energy. The high-frequency energy is imparted by applying a voltage across the electrode portions 22 adjacent to each other in the circumferential direction.

When the biological tissue in the vicinity of the edge of the puncture hole Hh is cauterized through the electrode portion 22, a degenerated portion where the biological tissue is degenerated is formed in the vicinity of the edge. The biological tissue in the degenerated portion loses elasticity, and thus, the puncture hole Hh can maintain the shape enlarged by the expansion body 21.

After performing the maintenance treatment, the operator checks the hemodynamics again (S8). When the amount of blood passing through the puncture hole Hh reaches a desired amount, the operator contracts the expansion body 21, stores the expansion body 21 into the storage sheath 25, and then, removes the expansion body 21 from the puncture hole Hh. Furthermore, the operator removes the entire medical device 10 from the living body to the outside, and ends the treatment.

Figure 12:
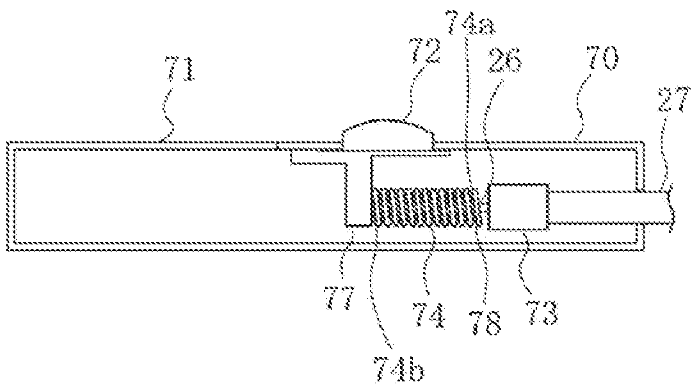
FIG. 12 is a front view illustrating an internal structure of a hand operation unit according to a first modification.

Next, a first modification of the hand operation unit will be described. As illustrated in FIG. 12, a hand operation unit 70 according to the first modification includes a pulling operation unit 72 in a housing 71, and an outer tube 27 is fixed to an outer tube holding portion 73 in the housing 71. A pulling shaft 26 extending to the proximal side from the outer tube holding portion 73 has a pulling shaft-side fixing portion 78 at the proximal end part to which a distal end part 74*a* of a buffer portion 74 is fixed. The pulling operation unit 72 includes a pulling operation unit-side fixing portion 77 extending into the housing 71 to which a proximal end part 74*b* of the buffer portion 74 is fixed. To insert a guide wire into the lumen of the pulling shaft 26, the proximal end part of the pulling shaft 26 may be extended from the pulling shaft-side fixing portion 78 and led out in the proximal direction from the proximal end of the housing 40. In this case, the pulling shaft-side fixing portion 78 is also disposed at the proximal end part of the pulling shaft 26 in terms of the entire pulling shaft 26.

Figure 13:
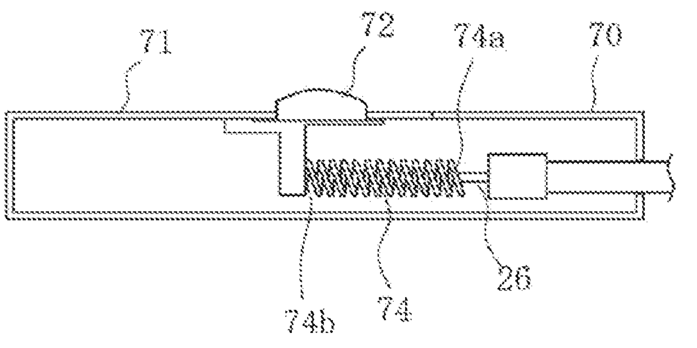
FIG. 13 is a front view illustrating the internal structure of the hand operation unit according to the first modification, and illustrates a state after the pulling operation.

When the pulling operation unit 72 is operated to slide toward the proximal side, the pulling shaft 26 moves toward the proximal side, and the buffer portion 74 is elastically deformed in the extending direction, as illustrated in FIG. 13. In this case, when the biological tissue is thick or hard, the buffer portion 74 is elastically deformed more largely (to a greater extent) in the extending direction, so that the biological tissue can be stably clamped by the expansion body 21 even if the movement amount of the pulling operation unit 72 is constant.

In the present modification, the proximal end part of the pulling shaft 26 may extend and be fixed to at least the pulling operation unit-side fixing portion 77 of the pulling operation unit 72, and a part or the whole of the pulling shaft 26 may be a buffer portion elastically deformable along the axial direction.

Figure 14:
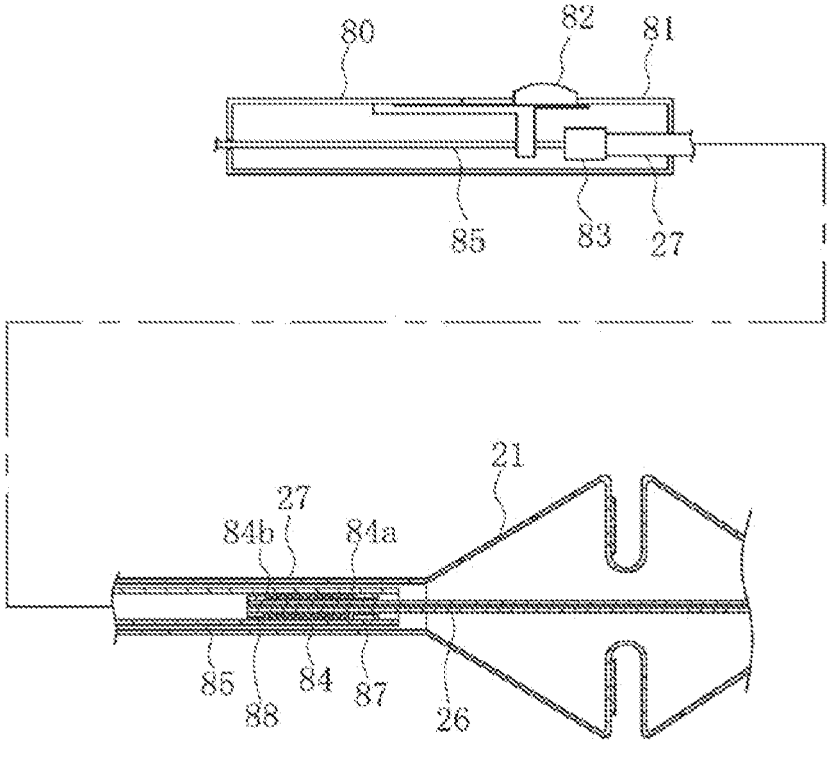
FIG. 14 is a front view illustrating an internal structure of a hand operation unit according to a second modification, and an enlarged cross-sectional view of the vicinity of a distal end of a shaft portion.

Next, a second modification of the hand operation unit will be described. As illustrated in FIG. 14, a hand operation unit 80 according to the second modification includes a pulling operation unit 82 in a housing 81, and an outer tube 27 is fixed to an outer tube holding portion 83 in the housing 81. An intermediate shaft 85 is drawn out or extends to the proximal side with respect to the outer tube 27. The intermediate shaft 85 extends to the vicinity of the distal end part 30 of the shaft portion 20 and has a pulling operation unit-side fixing portion 87 at the distal end. A distal end part 84*a* of the buffer portion 84 disposed in the shaft portion 20 is fixed to the pulling operation unit-side fixing portion 87. The pulling shaft 26 has a pulling shaft-side fixing portion 88 for fixing the proximal end part 84*b* of the buffer portion 84 at the proximal end part, and extends to the distal side from the pulling shaft-side fixing portion 88.

When the pulling operation unit 82 is operated to slide to the proximal side, the intermediate shaft 85 moves to the proximal side, and the pulling shaft 26 moves to the proximal side while the buffer portion 84 disposed in the shaft portion 20 is elastically deformed in the compression direction. In this case, when the biological tissue is thick or hard, the buffer portion 84 is elastically deformed more largely in the compression direction, so that the biological tissue can be stably clamped by the expansion body 21 even if the movement amount of the pulling operation unit 82 is constant. In this manner, the buffer portion 84 may be disposed inside the shaft portion 20.

Figure 15:
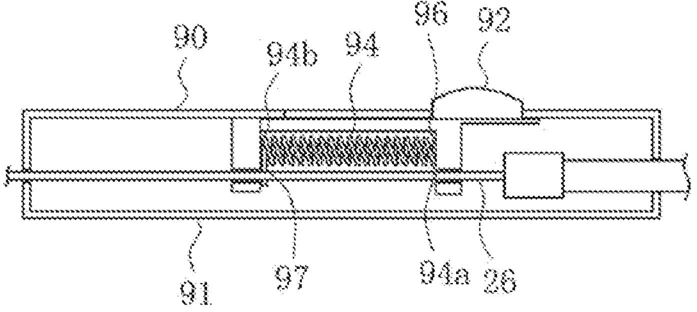
FIG. 15 is a front view illustrating an internal structure of a hand operation unit according to a third modification.

Next, a third modification of the hand operation unit will be described. As illustrated in FIG. 15, a hand operation unit 90 according to the third modification includes a pulling operation unit 92 in a housing 91. A buffer portion 94 is disposed not coaxially with but parallel to a pulling shaft 26 at a different position in the radial direction. The pulling operation unit 92 includes a pulling operation unit-side fixing portion 96 that fixes a distal end part 94*a* of the buffer portion 94, and the pulling shaft 26 includes a pulling shaft-side fixing portion 97 that fixes a proximal end part 94*b* of the buffer portion 94. In order to dispose the buffer portion coaxially with the pulling shaft 26, it is necessary to fix the buffer portion and the pulling shaft 26 after the pulling shaft 26 is entirely inserted into the buffer portion. On the other hand, when the buffer portion 94 is disposed parallel to the pulling shaft 26 at a different position in the radial direction as in the hand operation unit 90 according to the third modification, it is only sufficient that the pulling shaft-side fixing portion 97 is attached to the pulling shaft 26 from the side, and the buffer portion 94 is fixed to the pulling shaft-side fixing portion 97, so that the assembly can be facilitated. In the present modification, a plurality of buffer portions 94 may be provided parallel to each other.

As described above, the medical device 10 according to the present embodiment includes: the expansion body 21 expandable and contractible in the radial direction; the shaft portion 20 that is elongated and includes the distal end part 30 including the proximal end fixing portion 31 to which the proximal end of the expansion body 21 is fixed; and the hand operation unit 23 disposed on the proximal side of the shaft portion 20, in which the shaft portion 20 includes the pulling shaft 26 that moves in the axial direction to compress the expansion body 21 in the axial direction, the hand operation unit 23 includes the pulling operation unit 41 that moves the pulling shaft 26 in the axial direction, and the pulling shaft 26 and the pulling operation unit 41 are connected to each other with the buffer portion 43 interposed therebetween, the buffer portion 43 being elastically deformable along the axial direction of the pulling shaft 26. In the medical device 10 configured as described above, the pulling shaft 26 is pulled by the pulling operation unit 41 via the buffer portion 43. Therefore, when the pulling operation unit 41 is operated to move by a certain amount, the buffer portion 43 is elastically deformed according to the thickness and hardness of the biological tissue with which the expansion body 21 is in contact, and thus, a constant pulling force can be applied to the expansion body 21 regardless of the state of the biological tissue. Accordingly, the biological tissue can be stably held and expanded by the expansion body 21.

The buffer portion 43 may include a distal end part 43*a* and a proximal end part 43*b* on a side opposite to the distal end part 43*a*, the pulling operation unit 41 may include a pulling operation unit-side fixing portion 66 fixed to one of the distal end part 43*a* and the proximal end part 43*b* of the buffer portion 43, the pulling shaft 26 may include a pulling shaft-side fixing portion 67 fixed to another of the distal end part 43*a* and the proximal end part 43*b* of the buffer portion 43, and the pulling operation unit-side fixing portion 66 and the pulling shaft-side fixing portion 67 may be disposed along the axial direction of the pulling shaft 26. With this configuration, the pulling operation unit 41, the buffer portion 43, and the pulling shaft 26 can be compactly accommodated.

The pulling operation unit-side fixing portion 66 may be fixed to the distal end part 43*a* of the buffer portion 43, the pulling shaft-side fixing portion 67 may be fixed to the proximal end part 43*b* of the buffer portion 43, and the buffer portion 43 may be elastically deformed in a compression direction by moving the pulling operation unit 41 from the distal side to the proximal side along the axial direction of the pulling shaft 26. With this configuration, a constant pulling force can be applied to the expansion body 21 with a simple structure in which the buffer portion 43 is elastically deformed in the compression direction.

The buffer portion 43 may be a coil spring through which the pulling shaft 26 is insertable. With this configuration, the pulling shaft 26 and the buffer portion 43 can be coaxially disposed, whereby the structure in the hand operation unit 23 can be made compact.

The buffer portion 94 may be a single or a plurality of coil springs disposed in parallel with the pulling shaft 26. With this configuration, the buffer portion 94 can be attached to the pulling shaft 26 from the side, whereby assembly can be facilitated.

The pulling operation unit-side fixing portion 77 may be fixed to the proximal end part 74*b* of the buffer portion 74, the pulling shaft-side fixing portion 78 may be fixed to the distal end part 74*a* of the buffer portion 74, and the buffer portion 74 may be elastically deformed in an extending direction by moving the pulling operation unit 72 from the distal side to the proximal side along the axial direction of the pulling shaft 26. With this configuration, a constant pulling force can be applied to the expansion body 21 with a simple structure in which the buffer portion 74 is elastically deformed in the extending direction.

A part or whole of the pulling shaft 26 may be elastically deformable along the axial direction of the pulling shaft 26. With this configuration, the pulling shaft 26 can be used as the buffer portion, whereby the structure can be further simplified.

The buffer portion 43 may be disposed inside the hand operation unit 23. With this configuration, the structure of the shaft portion 20 can be prevented from being complicated.

The medical device disclosed here is not limited to the embodiments described above, and various modifications may be made by those skilled in the art within the technical idea of the present invention. For example, in the above-described embodiments, the buffer portion 43 is a coil spring, but the buffer portion only needs to be elastically deformable along the axial direction of the shaft portion 20, and may be rubber, a resin material, a bellows-like member, or the like.

This application is based on Japanese Application No. 2021-36374 filed on Mar. 8, 2021, the entire content of which is incorporated herein by reference.

The detailed description above describes embodiments of a medical device representing examples of the new medical device disclosed here. The invention is not limited, however, to the precise embodiments and modifications and variations described. Changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST

10 medical device
11 guide wire
20 shaft portion
21 expansion body
22 electrode portion
23 hand operation unit
25 storage sheath
26 pulling shaft
27 outer tube
30 distal end part
31 proximal end fixing portion
33 distal end fixing portion

35 distal member
40 housing
41 pulling operation unit
42 outer tube holding portion
43 buffer portion
43*a* distal end part
43*b* proximal end part
50 wire portion
51 recess
51*a* bottom portion
51*b* reception space
52 proximal-side upright portion
53 distal-side upright portion
55 outer peripheral portion
56 back support portion
56*a* receiving surface
57 arm portion
57*a* bent portion
60 slit
61 outer tube insertion opening
62 pulling shaft insertion opening
65 slide portion
66 pulling operation unit-side fixing portion
67 pulling shaft-side fixing portion

What is claimed is:

1. A medical device operated by an operator to cauterize an edge of a puncture hole in a living body, the medical device comprising:

an expansion body positionable in the puncture hole in the living body and having opposite axial end portions that are relatively movable so that as the opposite axial end portions approach one another the expansion body expands radially outwardly towards the edge of the puncture hole in the living body, and as the opposite axial end portions move away from each other the expansion body contracts radially inwardly away from the edge of the puncture hole in the living body, the opposite axial end portions including a proximal end portion and a distal end portion;

an energy transfer element positioned on the expansion body and movable into contact with the edge of the puncture hole in the living body as the expansion body expands radially outwardly to transfer energy to the edge of the puncture hole in the living body and cauterize the edge of the puncture hole;

an elongated outer tube having a distal end portion fixed to the proximal end portion of the expansion body;

a shaft positioned in the elongated outer tube, the shaft being axially movable in an axial direction relative to the elongated outer tube and including a distal portion that extends distally beyond the distal end portion of the elongated outer tube, the distal portion of the shaft being configured to pull the distal end portion of the expansion body in a proximal direction by pulling the shaft in the proximal direction;

an elastically deformable part that moves together with the shaft in the axial direction and that is elastically deformable in the axial direction; and an upstanding operation part that is engageable by the operator to slidably move the upstanding operation part in a proximal direction, the upstanding operation part being disposed on a proximal side of the shaft opposed to the distal portion of the shaft; and wherein the upstanding operation part is connected to the shaft via the elastically deformable part positioned between the shaft and the upstanding operation part so that sliding movement of the upstanding operation part in the proximal direction causes axial movement of the distal portion of the shaft in the proximal direction via the elastically deformable part, with the axial movement of the distal portion of the shaft in the proximal direction causing the opposite axial end portions of the expansion body to approach one another so that the expansion body expands radially outwardly.

2. The medical device according to claim 1, wherein the shaft passes through the elastically deformable part.

3. The medical device according to claim 1, wherein the elastically deformable part includes a distal end portion and a proximal end portion, the distal end portion of the elastically deformable part being fixed to the upstanding operation part by way of a fixing portion extending from the upstanding operation part, and the proximal end portion of the elastically deformable part being fixed to the shaft.

4. The medical device according to claim 1, wherein the elastically deformable part includes a distal end portion and a proximal end portion, the distal end portion of the elastically deformable part being fixed to the shaft, and the proximal end portion of the elastically deformable part being fixed to the upstanding operation part by way of a fixing portion extending from the upstanding operation part.

5. The medical device according to claim 1, wherein the shaft passes through a housing having an interior, the elastically deformable part being located in the housing, the upstanding operation part being slidably mounted on the housing.

6. The medical device according to claim 1, wherein the shaft passes through a housing having an interior, the upstanding operation part being slidably mounted on the housing, the elastically deformable part being located distal of the housing.

7. The medical device according to claim 1, wherein the energy transfer element positioned on the expansion body comprises a plurality of spaced apart electrodes positioned on the expansion body.

8. The medical device according to claim 7, wherein the expansion body includes a recess that is recessed radially inward of the expansion body and that includes a bottom, the plurality of electrodes being positioned on opposite sides of the recess.

9. The medical device according to claim 1, wherein the elastically deformable part has a central axis and the shaft has a central axis, the central axis of the elastically deformable part being spaced radially outwardly of the central axis of the shaft.

10. A medical device operated by an operator to cauterize a puncture hole in a living body, the medical device comprising:

an expansion body positionable in the puncture hole in the living body and having opposite axial end portions that are relatively movable so that as the opposite axial end portions approach one another the expansion body expands radially outwardly towards the edge of the puncture hole in the living body, and as the opposite axial end portions move away from each other the expansion body contracts radially inwardly away from the edge of the puncture hole in the living body, the opposite axial end portions including a proximal end portion and a distal end portion;

an electrode positioned on the expansion body to contact an edge of the puncture hole in the living body as the expansion body expands radially outwardly to cauterize the edge of the puncture hole;

an elongated outer tube having a distal end portion fixed to the proximal end portion of the expansion body;

a shaft positioned in the elongated outer tube, the shaft being axially movable in an axial direction relative to the elongated outer tube and including a distal portion that extends distally beyond the distal end portion of the elongated outer tube and a proximal portion opposed to the distal portion in the axial direction;

a housing having an interior in which is inserted a proximal portion of the shaft;

a manually engageable part that is slidably mounted on the housing and that is manually engageable by the operator to slidably move the manually engageable part in a rearward direction relative to the housing, wherein the distal portion of the shaft is configured to pull the distal end portion of the expansion body in the rearward direction by pulling the shaft in the rearward direction, and wherein the manually engageable part is operatively connected to the shaft by way of an elastically deformable part so that sliding movement of the manually engageable part in the rearward direction causes movement of the distal portion of the shaft in the rearward direction via the elastically deformable part, with the movement of the distal portion of the shaft in the rearward direction causing the opposite axial end portions of the expansion body to approach one another so that the expansion body expands radially outwardly.

11. The medical device according to claim 10, wherein the elastically deformable part has one end fixed relative to the shaft and an opposite end fixed relative to the manually engageable part.

12. The medical device according to claim 10, wherein the elastically deformable part is a spring positioned distal of a proximal end of the housing and proximal of the distal end of the distal end portion of the elongated outer tube.

13. A medical device comprising:

an expansion body expandable and contractible in a radial direction, the expansion body possessing a proximal end;

a shaft portion that is elongated and includes a distal end part including a proximal end fixing portion to which the proximal end of the expansion body is fixed; a hand operation unit disposed on a proximal side of the shaft portion;

the shaft portion including a pulling shaft that is movable in an axial direction to compress the expansion body in the axial direction;

the hand operation unit including a pulling operation unit that moves the pulling shaft in the axial direction;

the pulling operation unit being connected via a buffer portion interposed between the pulling shaft and the pulling operation unit, the buffer portion being elastically deformable along the axial direction of the pulling shaft; and the pulling operation unit being axially movable in a proximal direction away from the expansion body, the buffer portion including an elastically deformable part having a proximal end part fixed to the pulling shaft.

14. The medical device according to claim 13, wherein the buffer portion includes a distal end part and a proximal end part on a side opposite to the distal end part, the pulling operation unit includes a pulling operation unit-side fixing portion fixed to one of the distal end part and the proximal end part of the buffer portion, the pulling shaft includes a pulling shaft-side fixing portion fixed to another of the distal end part and the proximal end part of the buffer portion, and the pulling operation unit-side fixing portion and the pulling shaft-side fixing portion are disposed along the axial direction of the pulling shaft.

15. The medical device according to claim 14, wherein the pulling operation unit-side fixing portion is fixed to the distal end part of the buffer portion, the pulling shaft-side fixing portion is fixed to the proximal end part of the buffer portion, and the buffer portion is elastically deformed in a compression direction by moving the pulling operation unit from a distal side to a proximal side along the axial direction of the pulling shaft.

16. The medical device according to claim 15, wherein the buffer portion is a coil spring through which the pulling shaft passes.

17. The medical device according to claim 15, wherein the buffer portion comprises at least one coil spring disposed in parallel with the pulling shaft.

18. The medical device according to claim 14, wherein the pulling operation unit-side fixing portion is fixed to the proximal end part of the buffer portion, the pulling shaft-side fixing portion is fixed to the distal end part of the buffer portion, and the buffer portion is elastically deformed in an extending direction by moving the pulling operation unit from a distal side to a proximal side along the axial direction of the pulling shaft.

19. The medical device according to claim 13, wherein the buffer portion is disposed inside the hand operation unit.

* * * * *